(12) United States Patent
Vidal et al.

(10) Patent No.: US 8,822,847 B2
(45) Date of Patent: Sep. 2, 2014

(54) DIGITAL SCALE ABLE TO MEASURE HUMAN WEIGHT AND DETERMINE SUITABLE DOSAGE OF A MEDICAMENT

(76) Inventors: Monique S. Vidal, Brooklyn, NY (US); Joel Vidal, New York, NY (US); Yael Vidal, New York, NY (US)

(*) Notice: Subject to any disclaimer, the term of this patent is extended or adjusted under 35 U.S.C. 154(b) by 242 days.

(21) Appl. No.: 13/417,261

(22) Filed: Mar. 11, 2012

(65) Prior Publication Data
US 2013/0233627 A1   Sep. 12, 2013

(51) Int. Cl.
*G01G 19/22* (2006.01)
*A01B 5/00* (2006.01)

(52) U.S. Cl.
USPC ......... 177/25.13; 177/245; 702/173; 128/923

(58) Field of Classification Search
USPC ............ 177/25.11–25.17, 25.19, 144, 245; 702/173; 128/908, 923, 924; 600/587
See application file for complete search history.

(56) References Cited

U.S. PATENT DOCUMENTS

| | | | | |
|---|---|---|---|---|
| 3,656,478 A | * | 4/1972 | Swersey ........................... | 604/66 |
| 4,038,973 A | * | 8/1977 | Moore ............................. | 600/22 |
| 4,844,187 A | * | 7/1989 | Jabero .............................. | 177/5 |
| 4,869,266 A | * | 9/1989 | Taylor et al. .................. | 600/587 |
| 6,038,465 A | * | 3/2000 | Melton, Jr. ................... | 600/407 |
| 6,180,893 B1 | * | 1/2001 | Salgo ............................. | 177/144 |
| 6,396,004 B2 | * | 5/2002 | Salgo ............................. | 177/144 |
| 6,538,215 B2 | * | 3/2003 | Montagnino et al. ...... | 177/25.16 |
| 6,781,067 B2 | * | 8/2004 | Montagnino et al. ...... | 177/25.13 |
| 6,844,506 B2 | * | 1/2005 | Nuesch et al. ............. | 177/25.11 |
| 7,314,451 B2 | * | 1/2008 | Halperin et al. ............. | 600/534 |
| 7,550,682 B2 | * | 6/2009 | Lawler et al. .............. | 177/25.16 |
| 7,555,436 B2 | * | 6/2009 | Brown .............................. | 705/2 |
| 7,736,318 B2 | * | 6/2010 | Cosentino et al. ........... | 600/508 |
| 8,083,676 B2 | * | 12/2011 | Halliday ....................... | 600/301 |
| 8,504,323 B2 | * | 8/2013 | Coradi .......................... | 702/173 |
| 2006/0241510 A1 | * | 10/2006 | Halperin et al. ............. | 600/534 |
| 2007/0118054 A1 | * | 5/2007 | Pinhas et al. ................. | 600/587 |
| 2008/0275349 A1 | * | 11/2008 | Halperin et al. ............. | 600/484 |
| 2012/0259378 A1 | * | 10/2012 | Heinrichs et al. ................ | 607/6 |

FOREIGN PATENT DOCUMENTS

| | | | | | |
|---|---|---|---|---|---|
| JP | 2002-200142 A | * | 7/2002 | ............... | A61J 3/00 |
| JP | 2004-267514 A | * | 9/2004 | ............... | A61J 3/00 |
| JP | 2006-6172414 A | * | 6/2006 | ............. | G06Q 50/00 |

* cited by examiner

*Primary Examiner* — Randy W Gibson

(57) ABSTRACT

Some embodiments of the present invention include a digital scale to measure a weight of a user who stands on the digital scale; and to calculate and convey to the user a dosage of a medicament which is appropriate for the user based on the measured user weight. The digital scale may determine the medicament dosage by performing a local query to a locally-stored medicament database which may be stored locally within the digital scale, and/or by performing a remote query to a remotely-stored medicament database which may be stored externally to the digital scale.

20 Claims, 6 Drawing Sheets

DIGITAL SCALE ABLE TO MEASURE HUMAN WEIGHT AND DETERMINE SUITABLE DOSAGE OF A MEDICAMENT

FIELD

Some embodiments of the invention are related to the field of measuring human weight.

BACKGROUND

A person may sometimes feel pain or may be sick, and may visit a physician or a medical clinic for medical checkup and to receive medical advice. The physician may check the patient, and may prescribe a medicament to the patient. The medicament may be an off-the-shelf drug or medicine that the patient may autonomously purchase without a prescription; or, the medicament may be a controlled substance or other drug which may require a pharmacist to dispense such medicament and only subject to providing a prescription.

The dispensed or purchased medicament may include a label or brochure indicating "directions", of how to use such medicament. The directions may be, for example, printed or written on a sticker attached to the medicament container by a pharmacist; or, may be printed on a box or container which contains the medicament; or, may be printed on a paper brochure which may be provided with the medicament.

SUMMARY

Some embodiments of the present invention may include a digital scale to measure a weight of a user who stands on the digital scale; and to calculate and convey to the user a dosage of a medicament which is appropriate for the user based on the measured user weight. The digital scale may determine the medicament dosage by performing a local query to a locally-stored medicament database which may be stored locally within the digital scale, and/or by performing a remote query to a remotely-stored medicament database which may be stored externally to the digital scale.

In some embodiments, for example, an apparatus may include: a weight measuring unit comprising one or more load cells to measure a weight of a user; a dosage determination module to determine a dosage of a medicament based on said weight of said user measured by the weight measuring unit; an output unit to convey said dosage of said medicament to the user.

In some embodiments, for example, the apparatus may be or may include a digital scale.

In some embodiments, for example, the apparatus may include: a display unit to display (a) the weight of the user measured by the weight measuring unit, (b) a name of said medicament, and (c) said dosage of said medicament determined by the dosage determination module based on said weight.

In some embodiments, for example, the apparatus may include: a display unit to concurrently display (a) the weight of the user measured by the weight measuring unit, (b) a name of said medicament, (c) the dosage of said medicament determined by the dosage determination module based on said weight, (d) a name of another medicament, and (e) a dosage of said other medicament determined by the dosage determination module based on said weight.

In some embodiments, for example, the apparatus may include: a memory unit to store data representing (A) names of a plurality of medicaments, and (B) dosing information items corresponding to said plurality of medicaments.

In some embodiments, for example, the apparatus may include: an input unit to allow a user to select a particular medicament name from said names of medicaments; wherein the dosage determination module is to determine a recommended dosage of said particular medicament based on the weight of the user measured by the weight measuring unit; wherein the output unit is to convey said recommended dosage of said particular medicament to the user.

In some embodiments, for example, the input unit may comprise: a microphone to receive a spoken utterance of the user, the utterance indicating said particular medicament name; wherein the apparatus further comprises a processor to process said spoken utterance and to extract said particular medicament name from said spoken utterance.

In some embodiments, for example, the apparatus may include: a wireless transceiver to receive, via a wireless communication link, one or more updates to said data stored in said memory unit.

In some embodiments, for example, the apparatus may include: a communication port to receive, via a wired communication link, one or more updates to said data stored in said memory unit.

In some embodiments, for example, the apparatus may include: a wireless transceiver to (i) send a query to a remote server, the query indicating (A) a user-selected medicament, and (B) the weight of the user as measured by the weight measuring unit; and (ii) receive from the remote server a response indicating a particular dosage of said user-selected medicament corresponding to said weight of the user.

In some embodiments, for example, the apparatus may include: a wireless transceiver to (i) send to a remote server a query indicating a user-selected medicament; and (ii) receive from the remote server a response indicating dosage information of said user-selected medicament corresponding to two or more weight range values; wherein the dosage determination module is to determine a recommended dosage of said user-selected medicament, based on (A) the weight of the user as measured by the weight measuring unit, and (B) the dosage information corresponding to the two or more weight range values received from the remote server.

In some embodiments, for example, the apparatus may include: a processor (A) to obtain local dosage information for a particular user-selected medicament based on a first, local, query towards a locally-stored medicament database internal to the apparatus; (B) to obtain remote dosage information for said particular user-selected medicament based on a second, remote, query towards a remotely-stored medicament database external to the apparatus; and (C) to transfer at least one of the local dosage information and the remote dosage information to the dosage determination module.

In some embodiments, for example, the apparatus may include: a single housing encapsulating the weight measurement unit, the dosage determination module, and the output unit.

In some embodiments, for example, the weight measurement unit is non-detachable from the dosage determination module.

In some embodiments, for example, the weight measurement unit is to transfer a value indicating the weight of the user to the dosage determination module via a wired link which is entirely internal to the apparatus.

In some embodiments, for example, the dosage determination module is to determine said dosage based exclusively on data stored internally within said apparatus, and without receiving wireless communication signals.

In some embodiments, for example, the dosage determination module is to determine said dosage based on a dual-query process which comprises both a local query to a locally-stored medicament database and a remote query to a remotely-stored medicament database.

Some embodiments may provide other and/or additional benefits and/or advantages.

BRIEF DESCRIPTION OF THE DRAWINGS

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

DETAILED DESCRIPTION OF SOME EMBODIMENTS

Figure 1:
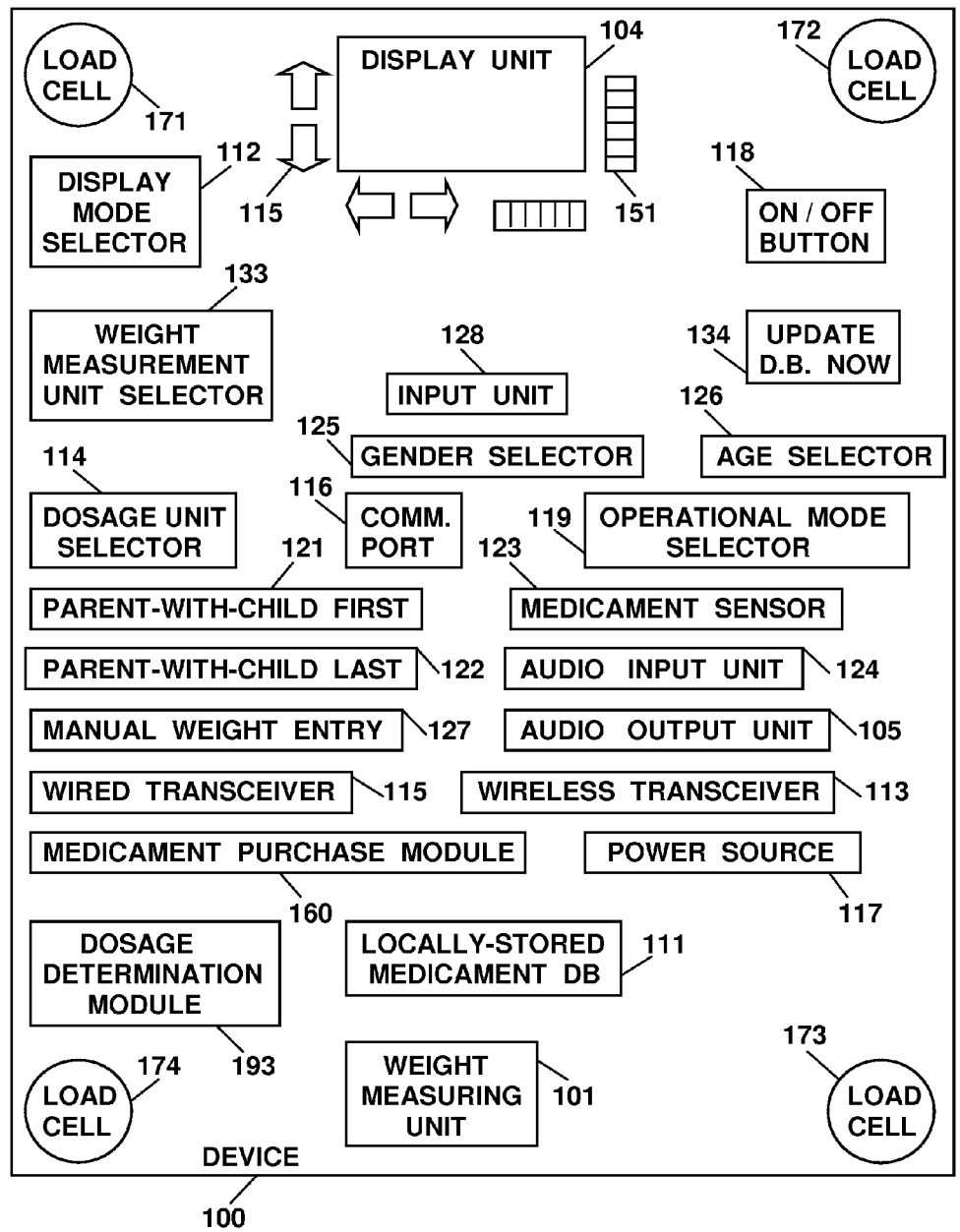
FIG. 1 is a schematic block diagram illustration of a device, in accordance with some demonstrative embodiments.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

The term "medicament" as used herein may include, for example, a medicine, a drug, a legal drug, a remedy, a controlled substance, an off-the-shelf medicament or drug, an over-the-counter medicament or drug, a drug available for purchase without a physician's prescription, a drug available for purchase only via a physician's prescription, a vitamin, a mineral, a supplement, a nutritional supplement, an enzyme, a probiotic or pre-biotic material, a capsule, a pill, a tablet, a caplet, a syrup, a liquid, a suspension, a drug dispensed or provided in liquid form, a drug dispensed or provided in solid form, a drug dispensed or provided in a bottle or a box or a container or a tube, a drug dispensed or provided in discrete units (e.g., discrete pills or capsules) or in non-discrete units (e.g., a liquid or syrup or gel or suspension stored in a bottle or container), a herbal ingredient or herbal medicine, a concoction, a specially-formulated drug or medicine, a herbal remedy, a homeopathic remedy, baby formula, baby food, a material that has FDA approval, a material that does not have FDA approval, a material sold in a pharmacy, a material sold in a supplement store or a vitamin store, a generic drug, a non-generic drug, a proprietary drug, a patented drug, and/or a combination of two or more of the above items, or the like.

The terms "user" and/or "person" as used herein may include, for example, a person who is sick or ill or in pain, a person who is healthy or not sick or not in pain, a person who is a patient, a person who is not considered a patient, a family member or a friend of a patient, a parent, a caregiver, or the like.

Although portions of the discussion herein may relate, for demonstrative purposes, to providing or conveying of output to a user by means of displaying on a display unit, some embodiments may utilize, alternatively or cumulatively, other means or methods to convey output to a user; for example, via voice or audio or speech, by playing or outputting an audio clip or video clip or audio/clip or animation clip or multimedia item, via vibration(s) (e.g., two vibration to indicate a dosage of two units), by printing information or output on a paper, or the like.

Although portions of the discussion herein may relate, for demonstrative purposes, to providing of input by a user by means of pressing one or more buttons, some embodiments may utilize, alternatively or cumulatively, other means or methods to allow a user to provide input, for example, by receiving audio input (e.g., speech, utterances, voice commands) and decoding such audio input (e.g., using speech-to-text converter or other recognizer), by receiving input via a physical keyboard or a physical keypad, via a virtual keypad or a virtual keypad (e.g., displayed on a screen or a touch-screen), via a touch-screen or a multi-touch screen, via one or more buttons or sliders or rollers or other mechanical components, by a pointing device (e.g., mouse, joystick, cursor keys, arrow keys, up/down keys, left/right keys, touch-pad), by detecting or sensing or interpreting user's gestures or movements (e.g., the user moving or dragging one or more fingers over a touch-screen, or performing a gesture with finger(s) on a touch-screen), or the like.

The applicants have realized that there does not exist a single device, an all-in-one device, an integrated device, an autonomous device, or a stand-alone device, which can measure a person's weight as well as determine and display a medicament dosage based on the measured weight.

The applicants have further realized that, particularly when a child is sick, a parent or caregiver may be overwhelmed or busy or distracted (e.g., if the child has fever or is in pain and is crying or screaming); and can make a human error in reading a dosage label or a dosage directions brochure which may be provided by a drug manufacturer. Further, such brochure or label or drug-container may be misplaced or lost, or may be soaked with a liquid that makes the printed text blurry or unreadable.

The applicants have also realized that a user (e.g., a parent, or a senior person, or a teenager) may mistakenly or accidentally read the wrong line in a dosage chart, and due to a human error may give (or may take) a medicament at a wrong dosage, a harmful dosage, an excessive dosage, or an insufficient dosage.

The applicants have further realized that some users do not know their own weight (entirely, or accurately), or the weight of the child; and some users may assume a wrong weight for themselves or for their child, thereby leading such user to manually calculate a wrong dosage or an inappropriate dosage for taking or for giving. Furthermore, some users may be too lazy or too busy or too tired or too weak (e.g. if the user himself is sick or ill or in pain), for correctly performing two (or more) operations of measuring a person's weight (the user's weight, or a child's weight) and correctly determining the appropriate drug dosage for the measured weight (e.g., due to being sick or ill themselves, or due to being distracted because a sick child is in pain or is crying).

Some embodiments may include a scale, for example, a digital scale able to measure or estimate a person's weight, mass, or gravitational mass; and able to determine, calculate and convey to the user a suggested or recommended or appropriate dosage, or a required dosage, of one or more medicaments to such person, based on the measured weight.

In some embodiments, a person may stand on the digital scale; and the digital scale may measure the weight of that person. The digital unit may then display to the person the measured weight; and may further display to the user (e.g. on a display unit integrated within the digital scale) a list of one or more medicaments, such that for each medicament on such list, the digital scales may display the name of a medicament and a dosage information for that medicament according to the measured weight.

In some embodiments, the digital scales may search a locally-stored and/or remotely-stored database, which may store names of medicaments, together with the dosage of each medicament according to the weight (or other characteristics) of the person who is supposed to take the medicament. The digital scales may look-up such database, and may convey to the user the dosage information for a user-selected medicament, or for one or more common or popular medicaments.

Reference is made to FIG. 1, which is a schematic illustration of a device 100 in accordance with some demonstrative embodiments of the invention. Device 100 may be implemented, for example, as digital weighing scales having additional and advanced features and able to assist a person in dosing of a medicament, as described herein.

Device 100 may include, for example, a weight measuring unit 101, a memory unit 102, a processor 103, a display unit 104, and an audio output unit 105.

Device 100 may include a weight measurement unit 101, able to measure or detect or estimate or sense or calculate the weight (or gravitational weight, or mass, or gravitational mass) of a user. In some embodiments, for example, the user may step on, or stand on, a generally-horizontal surface of device 100. Weight measurement unit 101 may operate, for example, by using a spring scale mechanism (e.g., able to measure weight, or tension force, or compression force, based on a distance that a spring deflects under a load); by measuring a torque of one arm relative to, or in balance with, a standard reference weight; by using a load cell; by using a strain gauge; or the like.

In some embodiments, for example, weight measurement unit 101 may operate as follows: when the user steps onto the top flat surface, a series of levers and brackets, or a stainless steel tray, beneath the surface of the scale distributes the weight evenly across a load cell (or one or more load cells); such that, regardless of where the user stands, the scale may correctly measure the user's weight. Any weight applied to the scale pushes down on one end (the higher side) of an internal load cell, which may be a metal beam that moves in relation to the user's weight. The lower side of the load cell may be attached to a strain gauge. As pressure is applied to the higher side of the load cell, it may shift slightly downward, causing the lower side of the load cell to move in such a way that it may bend the strain gauge beneath it. Any "strain" applied to the strain gauge by the load cell beam, triggers electrical charges in accordance to the amount of electrical resistance. For example, the greater the strain, the more intense the signal. Optionally, four strain gauges may be used, structured as a "Wheatstone bridge" to measure resistance using a bridge-like circuit design of four resistors (e.g., three known resistors and one unknown resistor). A microprocessor or controller or logic circuitry (e.g., processor 103 or other controller) may receive an analog signal from the strain gauge, and may converts it into digital information, which may be then sent to a display unit to convey the measured weight to the user. Optionally, weight measuring unit 101 may include, or may be associated with, four load cells 171-174, which may be located, for example, in proximity to the four respective corners or a generally square-shaped (or rectangular) device 100.

In some embodiments, weight measurement unit 101 may utilize a load cell which may be a transducer able to convert a force into electrical signal. The conversion may be indirect, and may be performed in two stages. Through a mechanical arrangement, the force being sensed may deform a strain gauge. The strain gauge may measure the deformation (strain) as an electrical signal, for example, since the strain may change the effective electrical resistance of the wire. The load cell may optionally include four strain gauges in a Wheatstone bridge configuration. Load cells of one strain gauge (quarter bridge) or two strain gauges (half bridge) may also be used. The electrical signal output may be, for example, in the order of a few millivolts, and may be subject to amplification by an instrumentation amplifier. The output of the transducer may be plugged into an algorithm to calculate the force applied to the transducer. Other types of components may be used, for example, hydraulic (or hydrostatic) load cell(s), piezoelectric load cell(s), vibrating wire load cell(s), or the like.

In some embodiments, weight measurement unit 101 may include a load cell (or multiple load cells) which may be subject to "ringing" when subjected to abrupt load changes. This may stem from the spring-like behavior of some load cells, which may need to deform in order to measure the load; and as such, a load cell of finite stiffness may have spring-like behavior, exhibiting vibrations at its natural frequency. An oscillating data pattern may be the result of such "ringing". Optionally, ringing may be suppressed or reduced by one or more suitable means (e.g., passive means). Additionally or alternatively, a control system or logic circuitry may utilize an actuator to actively damp out the "ringing" of a load cell. Other suitable methods or means may be used in order to allow weight measurement unit 101 to correctly measure the weight of the user.

Memory unit 102 may include, for example, a storage unit, Flash memory, volatile memory, non-volatile memory, Random Access Memory (RAM), a Secure Digital (SD) memory card, a hard disk drive, a SIM card, a removable memory unit, a non-removable memory unit, or the like.

Processor 103 may include, for example, a general purpose processor, a specific-purpose or dedicated processor, a controller, a programmable processor, a Central Processing Unit (CPU), a Digital Signal Processor (DSP), circuitry, an Integrated Circuit (IC), a logic circuit, a logic component, a single-core or dual-core or quad-core or multiple-core processor or processing sub-system, a single threaded processor, a double threaded processor or a multithreaded processor, or the like.

Display unit 104 may include, for example, a screen, a Liquid Crystal Display (LCD) unit or screen, a color screen, a black-and-white or gray-scale screen, a touch-screen, an active matrix screen, a plasma screen, a Light Emitting Diode (LED) screen, an Organic LED (OLED) screen, or the like.

Audio output unit 105 may include, for example, one or more components able to generate or produce audio and/or speech. Audio output unit 105 may include, for example, one or more speakers, an audio jack able to output audio (e.g., to earphones or headphones), a sound card or synthesizer, or the like.

Weight measuring unit 101 may generate a value corresponding to the measured weight of the user ("weight value"). Then, processor 103 may store the weight value in memory unit 102.

Processor 103 may cause device 100 to output or convey the weight value to the user in one or more ways. For example, display unit 104 may display the weight value which the user may then read; and/or, audio output unit 105 may output a readout or a playback of the weight value an audible phrase (e.g., by using a text-to-speech converter or other suitable module or component).

In some embodiments, device 100 may include a locally-stored medicament database 111, which may include one or more records corresponding to one or more respective medicaments. Each record may include, for example, a name of the medicament (e.g., "Children's Tylenol Oral Suspension"; a name or indicator of a maker of the medicament (e.g., "McNeill"); and one or more data items indicating a recommended dosage of that medicament based on one or more patient characteristics (e.g., weight). In some embodiments, locally-stored medicament database 111 may include records and data about thousands or hundreds of medicaments; in other embodiments, locally-stored medicament database 111 may include records and data about a subset or a group of medicaments, for example, top-100 most popular or most commonly taken medicaments; in yet other embodiments, locally-stored medicament database 111 may include records and data about a set of medicaments having a common characteristic, for example, medicaments directed only to children, or medicaments directed to women, or medicaments directed to pregnant women, or medicaments directed to men, or medicaments directed to senior citizens, medicaments directed to diabetic patients or diabetic persons, medicaments directed to renal patients, medicaments directed to cancer patients, medicaments having a common certification or approval or ingredient (e.g., FDA-approved, or Kosher, or vegan, or gluten-free), or medicaments of only a particular brand or manufacturer, or a combination of the above. In some embodiments, optionally, a drug manufacturer may produce and/or provide, for a price or for free, device 100 implemented as a digital scale, such that the locally-stored medicament database 111 may include only medicaments sold or manufactured by that drug manufacturer (e.g., and not other drug manufacturers).

Table 1 shows a demonstrative record which may be stored in database 111, corresponding to one demonstrative medicament:

TABLE 1

| Medicament Name: | | Children's Tylenol Oral Suspension | |
|---|---|---|---|
| Weight (lb) | Age (years) | Dose (mL) | Dose (tsp) |
| Under 24 | Under 2 | Do Not Use | Do Not Use |
| 24-35 | 2-3 | 5 | 1 |
| 36-47 | 4-5 | 7.5 | 1.5 |
| 48-59 | 6-8 | 10 | 2 |
| 60-71 | 8-10 | 12.5 | 2.5 |
| 72-95 | 11 | 15 | 3 |
| Over 95 | 12 and over | Ask Doctor | Ask Doctor |

Processor 103 may search or query or look-up in database 111, in order to obtain dosage data corresponding to the weight value as measured by weight measurement unit 101. For example, weight measurement unit 101 may measure a weight of 38 pounds for the user; the weight value may be 38 (representing 38 pounds); and processor 103 may access the row or field, in the record shown in Table 1, which indicate a corresponding dose of 7.5 milliliters or 1.5 teaspoons.

Processor 103 may then cause device 100 to output or display or present or convey one or more indications of the dosage information which corresponds to the measured weight value. For example, display unit 104 may display the name of the medicament (e.g., "Children's Tylenol Oral Suspension"), followed by (or in proximity to) the measured weight value (e.g., "38 pounds" or "38 lb") or a rounded weight value (e.g., displaying "38 pounds" if the weight value is 38.2, or, displaying "39 pounds" if the measured weight value is 38.9), and further followed by (or in proximity to) dosage information expressed in one or more dosage units (e.g., in milliliters and/or teaspoons, for example, displaying "7.5 milliliters" and/or "1.5 teaspoons").

Optionally, the information described above may be provided as audible output which may be generated by audio output unit 105, in addition to or instead of being displayed by display unit 104.

Figure 2:
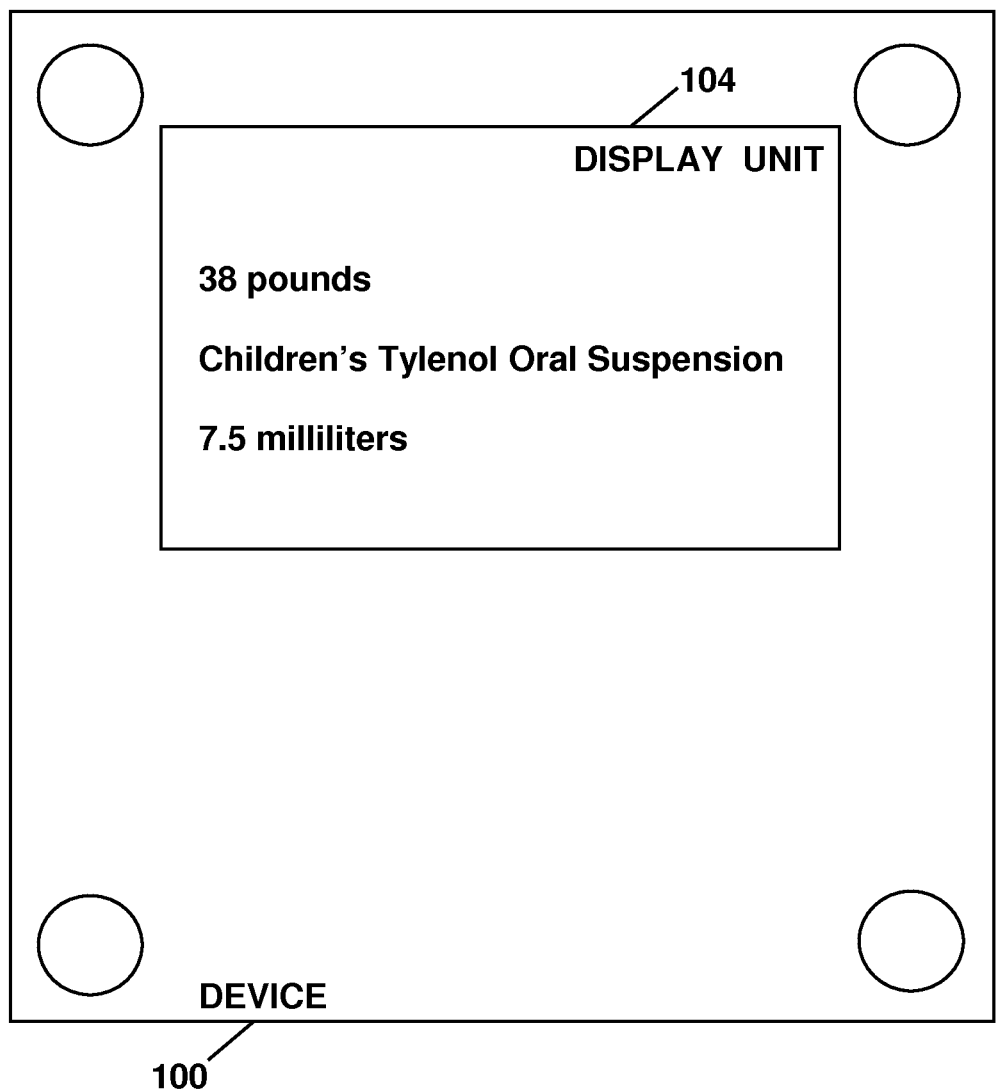
FIGS. 2-6 are schematic illustrations of the device, showing particularly some demonstrative content generated by the device and displayed on its display unit, in accordance with some demonstrative embodiments.

Reference is made to FIG. 2, which is a schematic illustration of device 100, in which display unit 104 displays, for demonstrative purposes, a measured weight of the user (e.g., who stands or stood on device 100); followed by or together with a medicament name; followed by or together with a dosage of that medicament for that weight value, expressed in milliliters.

Figure 3:
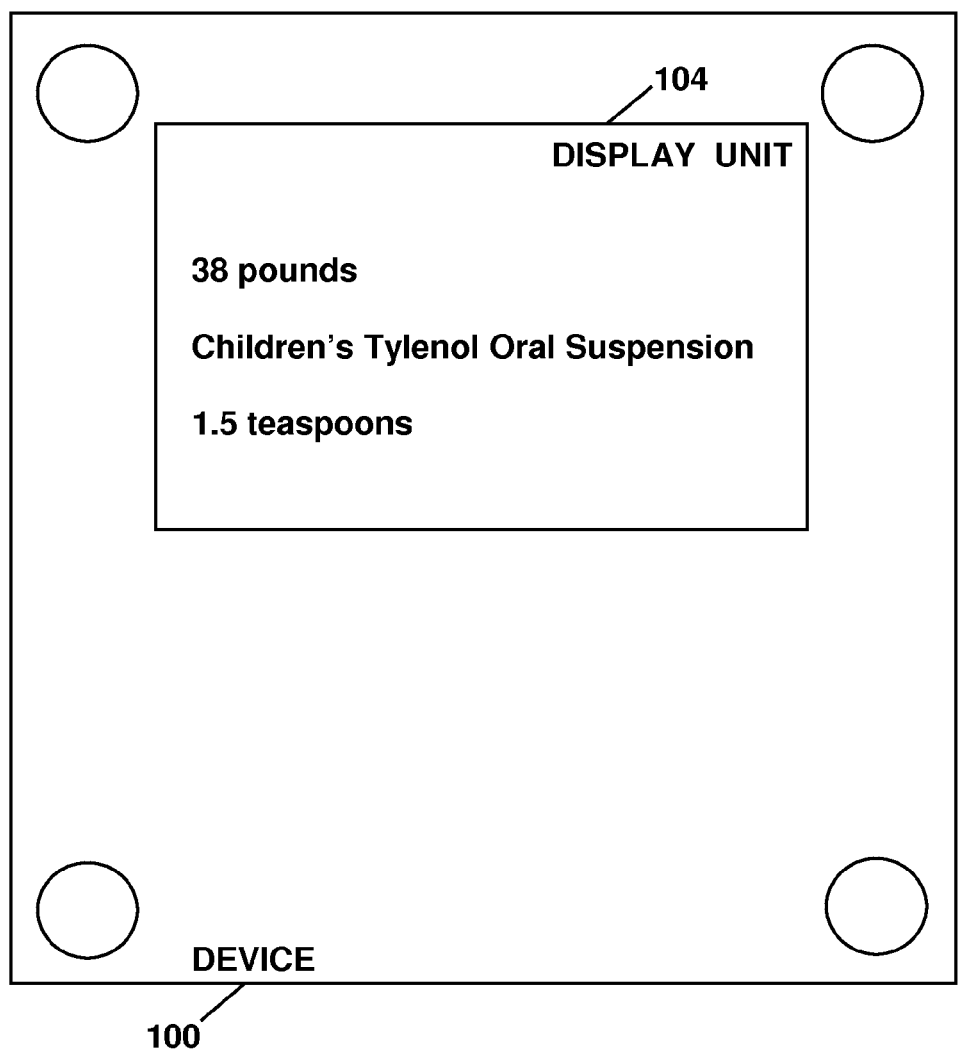

Reference is made to FIG. 3, which is a schematic illustration of device 100, in which display unit 104 displays, for demonstrative purposes, a measured weight of the user (e.g., who stands or stood on device 100); followed by or together with a medicament name; followed by or together with a dosage of that medicament for that weight value, expressed in teaspoons.

Figure 4:
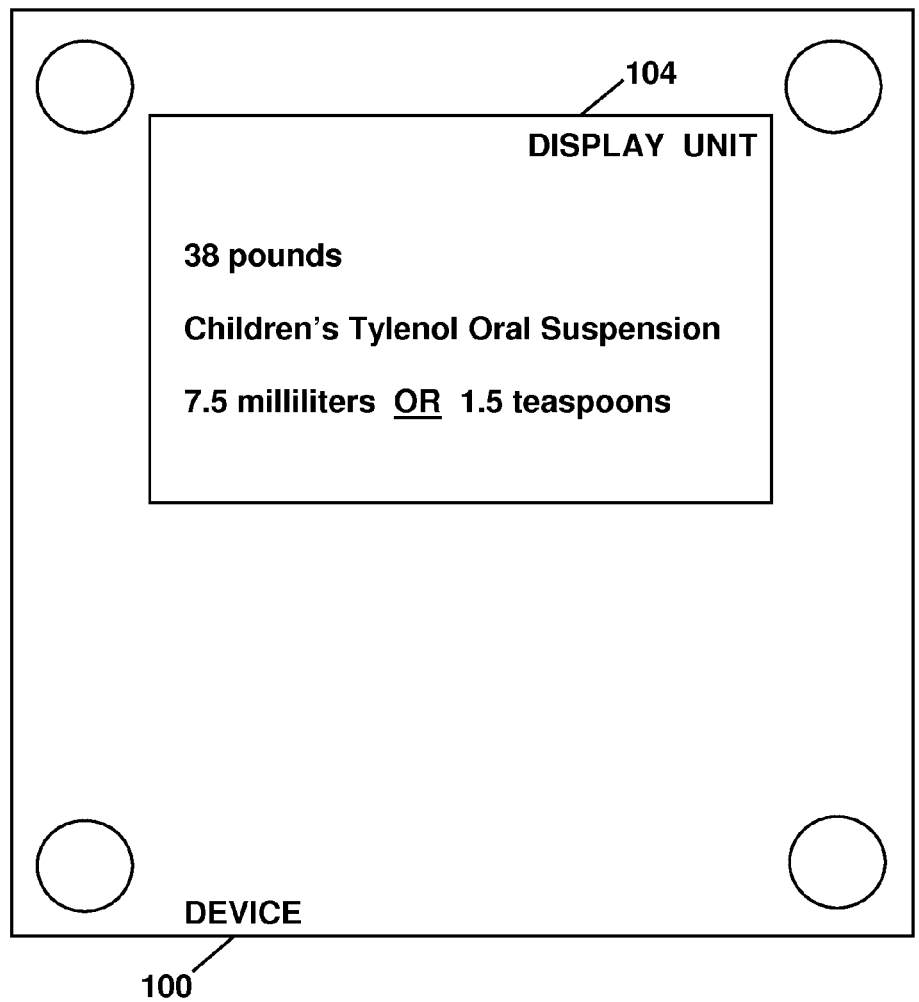

Reference is made to FIG. 4, which is a schematic illustration of device 100, in which display unit 104 displays, for demonstrative purposes, a measured weight of the user (e.g., who stands or stood on device 100); followed by or together with a medicament name; followed by or together with a dosage of that medicament for that weight value, expressed in milliliters and also expressed in teaspoons.

Optionally, a record of a medicament (e.g., stored locally in database 111) may store data indicating one or more notifications, alerts, warnings, timing information, allergy information, special instructions or directions, or other data pertaining to the ingredients, usage, dosage, handling, storage and/or effects of that medicament. Such data items may include, for example, "Take one dose every four hours", and/or "No more than three doses per day", and/or "Take with food", and/or "Take with water", and/or "Take before sleep", and/or "Take on empty stomach", and/or "Do not exceed", and/or "Store in fridge", and/or "Store at room temperature", and/or "Store in freezer", and/or "Shake well before use", or the like. Optionally, device 100 may convey to the user (e.g., by displaying on display unit 104, and/or by generating audio output through audio output unit 105) such additional information or data items.

Figure 5:
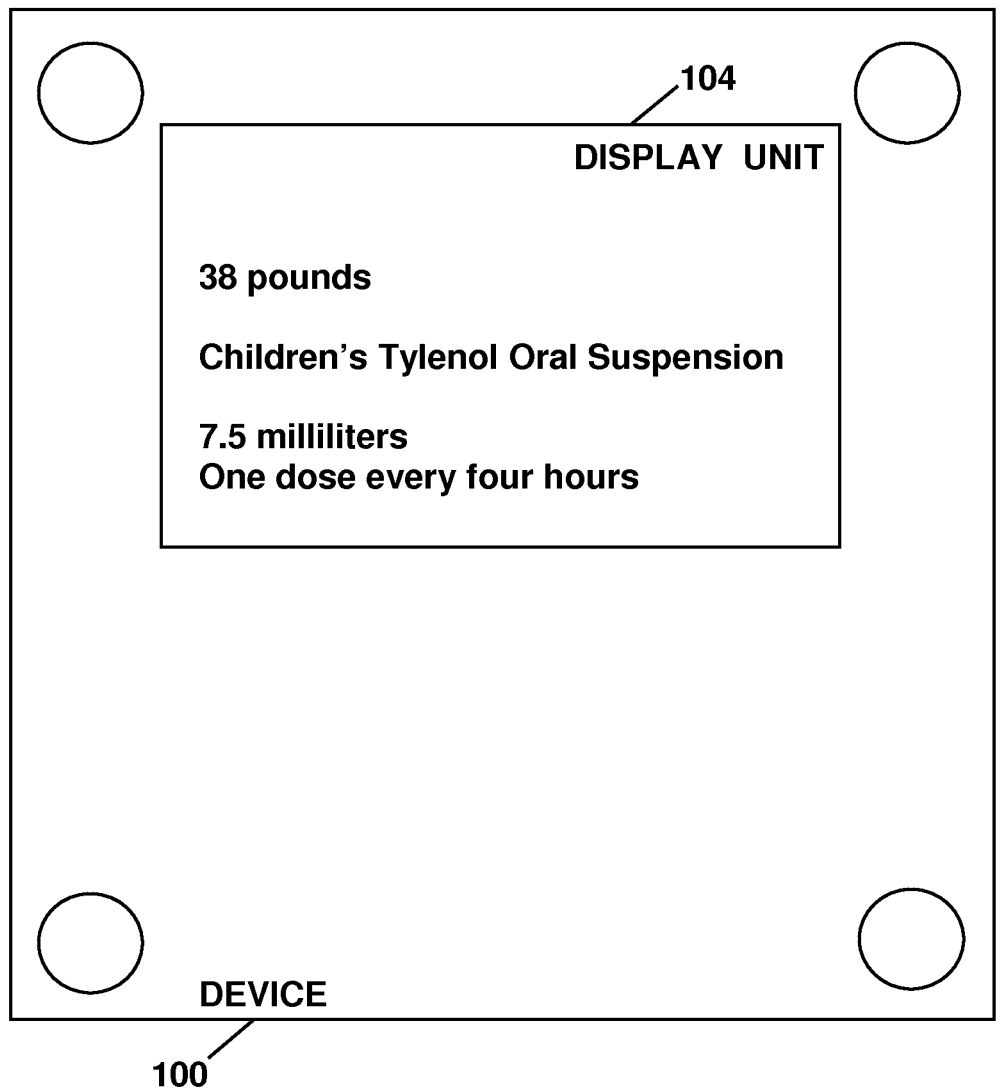

Reference is made to FIG. 5, which is a schematic illustration of device 100, in which display unit 104 displays, for demonstrative purposes, a measured weight of the user (e.g., who stands or stood on device 100); followed by or together with a medicament name; followed by or together with a dosage of that medicament for that weight value, expressed in milliliters; followed by a demonstrative "special instructions" data item stored in that medicament record.

In some embodiments, one or more operations which may be described herein with reference to processor 103, may be performed by a dosage determination module 193, which may be included in device 100 as a module or component, implemented using software and/or hardware. For example, dosage determination module 193 may receive the weight value from weight measurement unit 101, may perform the lookup or query or search in the locally-stored medicament database 111 (and/or in an external, remotely-stored medicament database), and may cause device 100 to convey to the user the dosage information corresponding to the measured weight, for one or more medicaments.

In some embodiments, display unit 104 may display all the information at once; for example, in an implementation which allows for a relatively large-size display unit 104. In other embodiments, display unit 104 may display the information in a scrollable window, such that the user may utilize a user interface (e.g., buttons, roller, slider, or the like) in order to scroll upward and downward (and/or sideways) to view, at a time, a portion of the entire information. In yet other embodiments, display unit 104 may autonomously or automatically display the information in a self-scrolling or self-refreshing manner, such that a different portion of the information is displayed for a short time (e.g., for five seconds) and is then replaced (entirely, or partially) by another portion of the information, and so forth. In some embodiments, a display mode selector button 112 (or other type of interface or input unit for user selection of a display mode) may be associated with display unit 104, and may allow the user to toggle or switch or select among multiple display modes, or to stop or pause or resume such self-scrolling or self-refreshing.

In some embodiments, device 100 may include a weight measurement unit selector button 133 (or other type of interface or input unit for user selection of a measurement unit), in order to allow the user to toggle or switch or select among multiple weight measurement units (e.g., pounds, ounces, kilograms, grams, stones). For example, a user may utilize the weight measurement unit selector button 113 in order to indicate that the user desires that all weight values are to be displayed by using pounds.

In some embodiments, device 100 may include a dosage unit selector button 114 (or other type of interface or input unit for user selection of a dosage unit), in order to allow the user to toggle or switch or select among multiple dosage units or method (e.g., milliliters, liquid ounces, teaspoons, tablespoons, cups). For example, a user may utilize the dosage unit selector button 114 in order to indicate that the user desires that all dosage information be displayed by using milliliters only. Optionally, multiple item selection may be supported by device 100; for example, the user may utilize the dosage unit selector button 114 in order to indicate that the user desires that all dosage information be displayed by using both milliliters and teaspoons.

In some embodiments, device 100 may produce output (e.g., to be displayed on display unit 104) which may include a series or list or set of medicaments, together with the dosing data for each such medicament for the particular weight value measured by weight measurement unit 101. Optionally, the list may be displayed on display unit 104. Optionally, a scrolling or browsing interface (e.g., arrow keys 115 or other cursor keys or browsing interface, or one or more rollers 151 able to be rolled or rotated by a user to indicate a user command to scroll the displayed portion upward or downward, or sideways) may be used in order to scroll or browse through the displayed list. In some embodiments, display unit 104 may be or may include a touch-screen or multi-touch screen or a tactile surface able to sense finger(s) touch and/or gesture thereon, and a user may utilize finger gestures (e.g., dragging a finger-tip across display unit 104) in order to scroll and/or browse through the list, for example, downward, upward, sideways, zoom in, zoom out, or the like.

Figure 6:
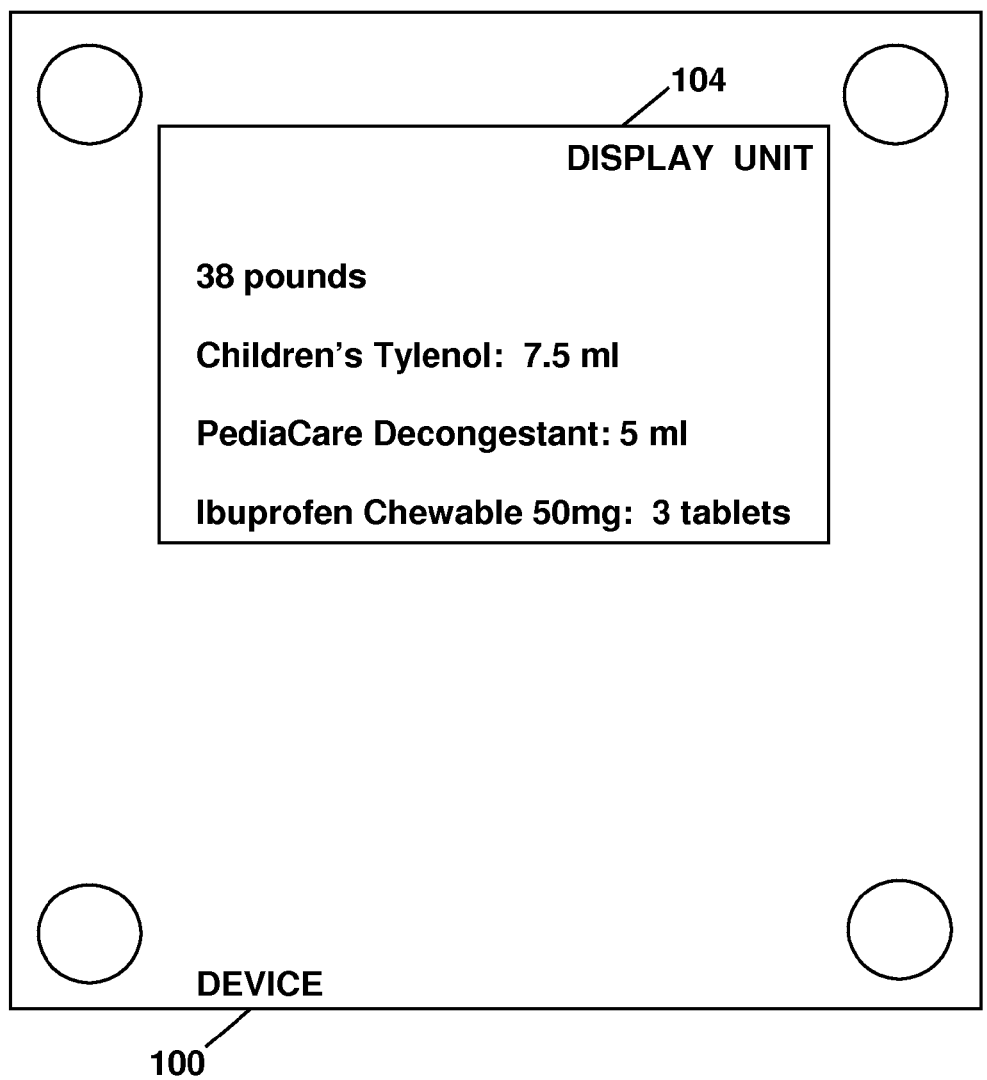

Reference is made to FIG. 6, which is a schematic illustration of device 100, in which display unit 104 displays, for demonstrative purposes, a measured weight of the user (e.g., who stands or stood on device 100); followed by or together with a list of medicament names (or, a portion or subset of such list), and for each such displayed medicament name, the dosage information based on the measured weight.

It is noted that in FIGS. 2-6, device 100 is shown with a focus on display unit 104 and its demonstrative content, and without showing other components and/or modules of device 100 (such as, for example, interface components, buttons, rollers, scroll units, or the like), for the sake of clarity and in order to not obscure the content of display unit 104 as demonstrated.

Referring again to Table 1 shown above, in some embodiments, a medicament record may include a value, a string, a flag, or other indication that for a certain weight or weight-range, dosage information cannot or may not be provided by device 100. For example, dosage data of "Do Not Use" may cause device 100 to output a warning to the user, via display unit 104 and/or via audio output unit 105 (e.g., a warning sound), that for the weight currently being measured (or most recently measured), a medicament may not be safely given or should not be given. Alternatively, dosage data of "Ask Doctor" may cause device 100 to output a notification to the user, via display unit 104 and/or via audio output unit 105 (e.g., a voice notification), that for the weight currently being measured (or most recently measured), a medicament may be provided but the dosage may be determined by a physician and device 100 may not provide dosage information or reliable dosage information.

In some embodiments, device 100 may optionally include a local-database updater module 112 able to receive updates and/or modifications to the content of medicament database 111. Such update data may include, for example, addition of a new medicament and its dosage data; removal of a medicament that was recalled or is not on the market; adding a warning notification to an existing medicament record; modifying dosage information of an existing medicament (e.g., due to a change in the formula of the medicament, or due to medical research developments); modifying name information of an existing medicament (e.g., due to renaming of a medicament); or the like. Device 100 may receive such database updates from a remote server via wireless communication and/or wired communication.

For example, device 100 may include a wireless transceiver 113, which may include, a wireless transmitter and/or wireless receiver, a cellular transceiver, a 2G transceiver, a 3G transceiver, a 4G transceiver, a 4G LTE transceiver, a Wi-Fi transceiver, a Wi-Max transceiver, a 3GPP transceiver, an IEEE 802.11 transceiver, an IEEE 802.16 transceiver, or the like. Optionally, wireless transceiver 113 may be associated with or may be coupled to one or more antennas, for example, an internal antenna, an external antenna, an internal/external antenna, an omni-directional antenna, a monopole antenna, a dipole antenna, an end fed antenna, a circularly polarized antenna, a micro-strip antenna, a diversity antenna, or the like. Wireless transceiver 113 may be used by device 100 in order to request and/or receive updates to locally-stored medicament database, for example, periodically (e.g., daily, twice per day, once per week, every other day, weekly, monthly, or the like), on demand (e.g., in response to a user command to device 100, entered via an input unit such as a keyboard or keypad or an "Update Database Now" button 134), upon a triggering event (e.g., if a threshold time period elapsed since a most-recent update was received), upon a person stepping onto device 100, or the like. In some embodiments, once a person steps onto device 100, processor 103 may check when was the last update received; and if the most recent database was received more than a predefined time period (e.g., more than a week ago, or more than a month ago), then processor 103 may initiate a process to request and/or receive update(s) from the remotely-stored database to locally stored medicament database 111.

In some embodiments, device 100 may request and/or receive such updates via a wired transceiver 115, and/or via one or more wired links, ports and/or cables. For example, device 100 may include a communication port 116, which may be or may include a USB port, a FireWire port, an Ethernet port, or other suitable type of port able to connect to an external source or cable or wire or link in order to allow transfer of data from device 100 outwardly and/or into device 100.

Device 100 may include a power source 117 able to provide power and/or voltage and/or current to one or more other components of device 100. Power source 117 may include, for example, one or more batteries or power cells, one or more rechargeable batteries or rechargeable power cells, one or more replaceable batteries, one or more AA batteries or AAA batteries or C batteries or D batteries or "button" batteries or Lithium batteries, or the like. In some embodiments, if power source 117 includes rechargeable components, charging may be performed via a cable or wire which may connect to an electric outlet, an electric power supply, a transformer, an external power source, or the like. In some embodiments, a dedicated port or plug or socket may be used for charging the power source 117; whereas in other embodiments, for example, communication port 116 may further operate as a port able to provide power to recharge the power source 117.

Optionally, device 100 may include an on/off button 118 able to switch or toggle device 100 among two or more modes of operation, for example, fully operable, non-operable (e.g., display unit 104 may not display anything even if a person stands on device 100), stand-by mode (e.g., display unit 104 does not current displays anything, but will become operative and will display weight information and/or medicament dosing information in response to a person stepping onto device 100), or the like.

Optionally, device 100 may include an operational mode selector 119 allowing the user to easily and/or efficiently switch or toggle or select among two or more modes of operation of device 100. For example, in a first demonstrative mode of operation, device 100 may operate only as digital scales, and may display or output only weight measurement information, and may not display or output any medicament dosing information or other medicament-related information. In a second demonstrative, mode of operation, device 100 may operate both as digital scales (e.g., and may display or output weight measurement information) as well as a medicament dosing facilitator able to display or output medicament dosing information or other medicament-related information which corresponds to the measured weight.

Optionally, device 100 may include one or more mechanisms to facilitate the weighting of a child who may resist a request to mount onto device 100, or who may not be able to steadily stand or rest upon device 100 for accurate or reliable weight measurement. In some embodiments, for example, device 100 may include a "Parent-With-Child First" button 121, which may be pushed or actuated in order to indicate to device 100 that a series of weighting operations are to be performed. Upon pressing or pushing or actuation of the "Parent-With-Child First" button 121, a parent (or grown up, or elder sibling, or sibling, or caregiver) may pick up and hold a child such that both the parent and the child are standing on top of device 100, or such that the parent (or caregiver) hold the child while the parents (alone) is standing on device 100. Weight measurement unit 101 may thus measure the combined weight of the parent and the child (denoted W1), and may store the weight value (W1) in memory unit 102. Then, the parent may signal to device 100 that the parent desires to weight only himself (or only herself), without the child; such signaling may be, for example, by pushing or pressing again the "Parent-With-Child First" button 121, or by stepping-off from device 100 and after a short time (e.g., after a time period of between 3 to 20 seconds) stepping-on onto device 100. The parent may safely let go of the child, or may remove the child away from device 100; and the parent may mount onto device 100 in order to measure, this time, only the parent's weight (denoted W2). Once the parent's weight is established, processor 103 may calculate the "net" weight of the child, by subtracting the recently-measured parent weight (W2) from the previously-measured combined weight of the parent and the child together (W1). Then, once the "net" weight of the child is calculated by processor 103, the "net" weight of the child may be displayed (on display unit 104) or may be otherwise conveyed to the user (e.g., via voice or speech, or an utterance such as "the child weighs 27 pounds"); and device 100 may proceed to obtain and to output one or more dosage values of one or more medicaments according to the calculated weight of the child.

In some embodiments, device 100 may utilize a reverse or different order of operations. For example, device 100 may include a "Parent-With-Child Last" button 122, which may be pushed or actuated in order to indicate to device 100 that a series of weighting operations are to be performed. Upon pressing or pushing or actuation of the "Parent-With-Child Last" button 122, a parent (or grown up, or elder sibling, or sibling, or caregiver) may step onto device 100 in order to allow device 100 to weigh only the parent. Weight measurement unit 101 may thus measure the weight of the parent (denoted W3), and may store the weight value (W3) in memory unit 102. Then, the parent may signal to device 100 that the parent desires that device 100 will measure now the combined weight of the parent with the child. Such signaling may be, for example, by pushing or pressing again the "Parent-With-Child Last" button 122, or by stepping-off from device 100 and after a short time (e.g., after a time period of between 3 to 20 seconds) stepping-on onto device 100. The parent may thus pick up the child or may hold the child or support the child, such that both the parent and the child stand on device 100 (or, such that the parent stands on device 100 while the parent holds the child). Accordingly, weight measurement unit 101 may now measure the combined weight of the parent and child (denoted W4). Then, processor 103 may calculate the "net" weight of the child, by subtracting the previously-measured parent weight (W3) from the recently-measured combined weight of the parent and the child together (W4). Then, once the "net" weight of the child is calculated by processor 103, the "net" weight of the child may be displayed (on display unit 104) or may be otherwise conveyed to the user (e.g., via voice or speech, or an utterance such as "the child weighs 27 pounds"); and device 100 may proceed to obtain and to output one or more dosage values of one or more medicaments according to the calculated weight of the child.

In some embodiments, optionally, device 100 may include a medicament sensor 123 able to identify a medicament presented by a user to the medicament sensor 123. Medicament sensor may be or may include, for example, one or more of the following components: (a) a barcode scanner or Universal Product Code (UPC) code scanner or Quick Response (QR) scanner, able to capture or read or scan or acquire, for example, a barcode or a code printed on a medicament or on a medicament container or on a medicament packaging, and able to identify the medicament that corresponds to the scanned or captured code or barcode by querying a local database and/or a remote database; (b) a camera or image sensor able to capture a photograph of the medicament (or its bottle, or its container, or its label, or its packaging), and able to identify the medicament that corresponds to the captured photograph by querying a local database and/or a remote database, and/or by utilizing Optical Character Recognition (OCR) to extract a medicament name from such photograph; (c) an audio input unit 124 (e.g., a microphone, or a microphone jack or socket or plug), allowing a user to utter or say a name of a medicament, such that processor 103 may perform speech-to-text conversion to extract the name of the medicament from the uttered speech or audio; or the like. Optionally, the user may hold the medicament in proximity to medicament sensor 123, or at a certain distance or range (e.g., twenty centimeters) or at a certain angel or position (e.g., the medicament name facing towards medicament sensor 123), to allow capturing or sensing of the information. In some embodiments, one or more illumination units (e.g., "flash" illumination, similar to a portable camera) may be included in device 100, in order to allow medicament sensor 123 to capture photographs and/or codes even in poor or non-optimal lighting conditions, or in order to improve the quality or reliability of captured images or codes. In some embodiments, medicament sensor 123 may autonomously operate responsive to the user placing a medicament in the field-of-view of medicament sensor 123. In other embodiments, medicament sensor 123 may operate responsive to the user pushing or pressing a button on device 100, for example, a "sense the medicament now" button, or responsive to the user uttering or saying a voice command (e.g., "sense the medicament package"). If the medicament is identified or recognized by device 100, and if the locally-stored medicament database stores data about that medicament (e.g., a record corresponding to that medicament), then, device 100 may selectively display on its display unit 104 only medicament name and dosing information for that particular medicine, and not for other medicaments. In some embodiments, if the medicament is identified or recognized by device 100, but locally-stored medicament database 111 does not store data about that medicament (e.g., due to storage capacity constraints, or because the particular medicament is new to the market), then processor 103 may initiate a process to lookup or query or search in a remotely-stored (external) database for such medicament (e.g., via wireless communication); optionally, processor 103 may then update the locally-stored medicament database 111, and/or may cause device 100 to output the dosage information corresponding to the measured weight value (e.g., selectively, by displaying the information on display unit 104 only the medicament name and dosing information for that particular medicine, and not for other medicaments). In some embodiments, the medicament may be presented to medicament sensor 123 before, during, and/or after the weighing of the user by device 100.

In some embodiments, processor 103 may query only the locally-stored medicament database 111 in order to obtain dosing information (e.g., for the particular weight value of the particular user). In other embodiments, processor 103 may utilize wireless transceiver 113 in order to query only a remotely-stored medicament database (e.g., hosted remotely, externally to device 100, in a remote server or a remote location), in order to obtain dosing information (e.g., for the particular weight value of the particular user. In yet other embodiments, processor 103 may utilize both the locally-stored medicament database and a remote (or external) database, for example, simultaneously, concurrently, at a certain order (e.g., local query followed by a remote query, or vice versa), or the like. In some embodiments, a local query may be performed only if a remote query fails or is slow or non responsive or not available (e.g., to allow device 100 to utilize a not-necessarily-fresh cache of medicament dosing information which may be stored locally); or, a remote query may be performed only if a local query fails (e.g., since the local query may be faster than a remote query); or, other suitable combinations of queries may be used. For example, a remote query (to a remote or external medicament database) may be initiated if a local query (to locally-stored medicament database 111) fails, or returns null results (e.g., if the requested or searched medicament does not have a record in the locally-stored medicament database 111. Optionally, a remote query may be performed while the user is standing on device 100 and after display unit 104 already presented (or while it still presents) dosing information for a particular weight (e.g., as reassurance or verification of the local data). In some embodiments, dual-querying (which may include both a local query of the locally-stored medicament database 111 and a remote query of a remotely-stored medicament database) may be selectively performed by device 100 based on one or more conditions or triggering events, for example, if the particular medicament is marked or pre-defined as such which requires dual querying (e.g., due to increased medical risk, due to being a controlled substance, or the like), if the user requests dual-querying (e.g., via a user command to device 100), on a random or pseudo-random basis (e.g., as a quality control or quality assurance measure of device 100), or the like.

In some embodiments, device 100 may optionally include a gender selector 125, which may be a button or interface allowing a user to indicate whether the medicament is intended to be taken by a female or a male. For example, a medicament may have different dosing, depending not only on the weight of the patient, but also on the patient's gender. This data may be included in the medicament's record in the locally-stored medicament database 111 (and/or in a remotely-stored medicament database), and may be taken into account by processor 103 prior to generating or displaying the dosing information.

In some embodiments, device 100 may optionally include an age selector 126, which may be a button or interface allowing a user to indicate the age (e.g., in years, or in months) or an age range (e.g., age range of 3 to 6 years, age range of 6 to 12 years, or the like), or the date of birth (e.g., 15 Feb. 2005), or the month of birth (e.g., February 2005), or the year of birth (e.g., 2005) of the person who intends to take the medicament. For example, a medicament may have different dosing, depending not only on the weight of the patient, but also on the patient's age or age-range. This data may be included in the medicament's record in the locally-stored medicament database 111 (and/or in a remotely-stored medicament database), and may be taken into account by processor 103 prior to generating or displaying the dosing information. In some embodiments, in which a user may enter or may input age data into device 100, then, memory unit 102 may store such age information for long term, together with a date-stamp of the date in which the data was entered by the user; and optionally, processor 103 may periodically update or advance the age data upon passage of time (e.g., measured by a real-time clock or internal clock, which may be part of processor 103, or may be coupled to processor 103, or may be part of device 100).

In some embodiments, device 100 may be able to assist a person in dosing of a medicament even without measuring the weight of the person who intends to take the medicament. In a demonstrative example, a child may sleep-over at grandparents house, and may have fever. Grandparents may call the parent to ask what amount of a particular fever-reducing medicament to dispense or serve or administer or give to the child. Grandparents may not have device 100, or may not have a box or label or brochure of the medicament (which may include dosing instructions). Over the phone, parent may take device 100, and may press a "manual weight entry" button 127, which may then allow the parent to convey to device 100 a known or estimated weight of the child. For example, parent may utilize the audio input unit 124 in order to say or utter "38 pounds", or, parent may use other type of an input unit 128 (e.g., a keyboard, a keypad, a virtual keyboard displayed on display unit 104, a virtual keypad displayed on display unit 104, a set of buttons or keys, or the like) in order to enter the weight into device 100. Then, processor 103 may determine the dosage based on the entered weight (rather than based on a measured weight), and may convey the dosing information to the parent, who may in turn convey the dosing information to the grandparents in order to remotely administer the drug to the child.

In some embodiments, a user may be able to perform a user profile definition with regard to device 100, for example, via a wireless connection to device 100, via a wired link to device 100, by using one or more buttons or interface components of device 100, or the like. The user profile may include one or more data items about the user, for example, gender, height, age, age range, date of birth (or month of birth, or year of birth), whether the user has particular characteristics (e.g., is or is not Kosher or vegan or gluten-free), whether the user has particular medical conditions (e.g., diabetics, cancer), or the like. The personal information may be stored in memory unit 102, and may be updated by the user from time to time if desired. Optionally, a user profile may be associated with a user name and/or a profile number, in order to allow multiple users (e.g., family members) to share among them a single device 100 (e.g., a discrete profile for each household member or family member); and the input interface of device 100 may allow a user to choose his or her profile from among the defined user profiles, as well as to create, add, modify, delete, or otherwise update one or more profile, or switch among profiles. Device 100 may take into account the data stored in the profile, when determining the dosage or information to be displayed or conveyed with regard to one or more medicaments.

In some embodiments, device 100 may facilitate and/or implement a process which allows a user to purchase one or more of the medicaments that are displayed (or otherwise conveyed) to the user through device 100. For example, the user may utilize an input interface of device 100 in order to enter payment method information (e.g., credit card or debit card information, credit card or debit card name, credit card or debit card number, credit card or debit card expiration date, name appearing on credit card or debit card, credit card or debit card security code, or the like); and the payment information may be stored, optionally encrypted, locally in memory unit 102 and/or remotely in an external secure server (e.g., accessible by device 100 via a wireless communication link). Furthermore, the user may utilize the input interface of device 100 in order to enter one or more merchants (e.g., pharmacy or store or shop) from which medicament(s) are to be ordered through the device; and may optionally indicate to device 100 a preferred shipping address and a preferred shipping method (e.g., same day shipping if available, overnight shipping, next day shipping, two-day shipping, ground shipping, or the like). Once the user sees a medicament name displayed on display unit 104, or, once the user selects one medicament out of multiple medicament names displayed on display unit 104, then, the user may click or press on a "purchase now" button 155 (or may otherwise enter a purchase command via other user interface components of device 100). In response, device 100 may initiate a process which places an order to purchase that medicament (or the user-selected medicament), from the preferred or default merchant (e.g., pharmacy), with the preferred or default payment method, with the preferred or default shipping address and shipping method, or the like. Optionally, the user may modify one or more of the order details (e.g., shipping address, shipping method, merchant identity, quantity of the medicament to be purchased, or the like), during the order process or after placing the initial "purchase now" command. In some embodiments, the user may indicate, in advance and/or during the order process, whether the ordered medicament should be dispensed immediately and shipped out to the user; or, should be dispensed but be placed on hold for a pick-up by the user at a later time rather than being shipped out to the user). Some embodiments may be able to handle and/or order a medicament which requires a physician's prescription for purchasing; for example, in response to a "purchase now" command, device 100 may automatically transmit to the merchant (e.g., pharmacy) a request that the pharmacy obtain the prescription from a default or preferred designated physician that the user of device 100 pre-defined or pre-designated; and/or, device 100 may automatically contact such pre-defined physician (e.g., by sending to the physician an email message, a text message, a voice or audio message, a fax, a pager or beeper message, or the like) in order to initiate a process in which the physician issues the required prescription and transfers the prescription to the preferred merchant (e.g., pharmacy). Optionally, a dedicated component or module in device 100, for example, a medicament purchase module 160, may be responsible for performing one or more of the operations described above and/or one or more of the operations which may be required to allow the user of device 100 to order or to purchase a selected medicament.

In some embodiments, memory unit 102 may store for long-term, data indicating medicaments purchased through device 100 (associated with the purchase date and other purchase information); and/or medicaments whose dosage was viewed through device 100 (associated with the viewing date). Device 100 may allow the user to browse, search, delete, edit, and/or view such stored data (in its entirety, or selectively item-by-item, or based on date or based on other parameters), and/or to export or transfer or transmit such data (or, selectively, one or more portions thereof) to a target or unit external to device 100, wirelessly or through a wired link.

In some embodiments, the term "medicament" as used herein may include baby formula or baby food; and device 100 may be used in order to assist a parent or caregiver with regard to feeding of a baby, an infant, a toddler, a child, or other person. For example, in some embodiments, device 100 may be used by a parent in order to weigh a baby; and device 100 may display or otherwise convey to the parent, in addition to the weight value of the child (e.g., "14 pounds"), also the amount of baby formula to be given to that child at that weight (e.g., per day, per feeding, or the like). Display unit 104 may display, for example, "Weight=14 pounds", followed by "Similac Baby Advance, 2 measuring-spoons of powder in 2.5 cups of water). Optionally, device 100 may store and/or track feedings done or measured, and may track and/or show the total amount of baby food (or calories, fat, carbohydrates, sodium, protein, or other ingredient) that the baby (or other consuming person) consumed and/or may consume, e.g., daily.

Some embodiments may include, or may be implemented as, a stand-alone digital scales device, similar to a "bathroom scales" device, able to directly measure the weight of the user via one or more load cells, and able to determine and display medicament dosage information corresponding to the measured weight. Some embodiments may be implemented as a single-apparatus solution or a self-containing apparatus, and not as a dual-component solution or s distributed solution (e.g., a smartphone or a tablet, which may be augmented by or connected to or associated with a scales surface). In some embodiments, all (or substantially all) the components of device 100 may be held, mounted, or otherwise placed within a single housing or box or container or a "bathroom scales" type of box.

In some embodiments, the term "medicament" may optionally include a drug or medicament or food intended to be given to a pet or animal (e.g., dog, cat, bird, gerbil, cow, horse, or the like); and device 100 may be adapted or pre-configured to measure weight of such animal(s) and to determine and convey a dosage of such medicament (e.g., drug or medicament or food intended to be given to such animal or pet) based on the measured animal weight and based on one or more queries to a local and/or a remote database of animal medicaments or animal foods.

In some embodiments, optionally, a tablet device (e.g., an Apple iPad, or a Motorola Xoom device) or a smartphone (e.g., an Apple iPhone, a Motorola Droid or Razr device, an Android device) may be constructed or configured or augmented to include one or more load cells, or four load cells (e.g., located in proximity to the four respective corners of such smartphone or tablet), thereby allowing to implement device 100 as a single-component or integrated solution which combines both a smartphone (or tablet) and a digital scales or "bathroom scales", optionally showing also medicament dosing information based on measured user weight, as detailed above. In other embodiments, device 100 may not include a smartphone, and may not include a tablet, and may not include any detachable or removable parts or units (entirely, or except for replaceable battery or batteries).

In some embodiments, updates to locally-stored medicament database 111 may be obtained and/or installed via a tangible token or article or storage article. For example, locally-stored medicament database 111 may be stored on a SD-card or on Flash memory card, which may be removable and/or replaceable. In some embodiments, device 100 may be purchased by a user together with subscription to a service, which may send to the user by mail or by courier updated SD-card(s) or updated Flash memory units for the user to install or replace (e.g., periodically, once per month, or the like). Optionally, a user of device 100 may purchase subscription to the update service which updates the content of locally-stored medicament database 111, and such updates may be delivered and/or installed via one or more other suitable ways, for example, via the Internet, by using wired and/or wireless communication links, by downloading such updates and installing them, by updating or upgrading or replacing firmware or software of device 100, or the like.

In some embodiments, optionally, the locally-stored medicament database 111 may store only names of medicaments (e.g., optionally coupled to or associated with a unique Medicament-ID number of string), and may not locally store any dosage information or directions (e.g., in order to "force" the device 100 to wirelessly obtain up-to-date dosage data from a remote server, to minimize errors and to eliminate the possibility of device 100 presenting to the user outdated data or wrong data or data about recalled medicaments). The dosage information may be obtained by device 100 through a wireless (or wired) link from a remote server, after device 100 submits (as a query) to such remote server the name of a medicament (and/or the Medicament-ID value) of a particular medicament that the user of device 100 selected by browsing or searching locally the database of medicament names.

In some embodiments, device 100 may include a wireless transceiver to receive, via a wireless communication link, one or more updates to the data stored in memory unit 102; and/or a communication port to receive, via a wired communication link, one or more updates to the data stored in memory unit 102.

In some embodiments, device 100 may determine the dosage of the medicament for the particular user being weighed, based on a query to a remote database, such that the query may include both a medicament name (or a unique medicament ID value) as well as a value indicating the measured user's weight. For example, device 100 may include a wireless transceiver to (i) send a query to a remote server, the query indicating (A) a user-selected medicament, and (B) the weight of the user as measured by weight measuring unit 111; and (ii) receive from the remote server a response indicating a particular dosage of the user-selected medicament corresponding to the weight of the user.

In some embodiments, device 100 may determine the dosage of the medicament for the particular user being weighed, based on a query to a remote database, such that the query may include only a medicament name (or a unique medicament ID value) but the query may not include the measured user's weight. For example, device 100 may include a wireless transceiver to (i) send to a remote server a query indicating a user-selected medicament; and (ii) receive from the remote server a response indicating dosage information of the user-selected medicament corresponding to two or more weight range values. Then, processor 103 (or a dosage determination module) may determine a recommended dosage of the user-selected medicament, based on (A) the weight of the user as measured by weight measuring unit 111, and (B) the dosage information corresponding to the two or more weight range values received from the remote server.

In some embodiments, device 100 may perform a dual-query or double-query process, which may include a local query followed by a remote query, or a remote query followed by a local query, or a remote query performed at least partially concurrently with a local query. For example, processor 103 may (A) obtain local dosage information for a particular user-selected medicament based on a first, local, query towards a locally-stored medicament database internal to device 100; and (B) obtain remote dosage information for that particular user-selected medicament based on a second, remote, query towards a remotely-stored medicament database external to device 100; and (C) transfer at least one of the local dosage information and the remote dosage information to a dosage determination module (or, to another module implemented by processor 103) for determining the dosage to be used.

In some embodiments, device 100 may be an all-in-one box or device, or an integrated device, or a non-modular device, such that device 100 may include a single housing encapsulating the weight measurement unit, the dosage determination module (or processor 103), and the output unit, and optionally also memory unit 102.

In some embodiments, device 100 may not be "broken" or "disassembled" or "separated" into a smartphone (or a tablet) and a digital scale. This may allow significant reduction in the cost of device 100, rather than attempting to achieve similar goals by attempting to link together a digital scale and a smartphone (or a tablet), and may further allow to keep device 100 at a small form-factor which resembles a "bathroom scales" unit. In some embodiments, the weight measurement unit of device 100 may be non-detachable and/or non-separable from the dosage determination module of device 100. In some embodiments, the weight measurement unit may be "hard-wired" to the dosage determination module via circuitry. In some embodiments, the weight measurement unit may transfer a value indicating the weight of the user to the dosage determination module via a wired link which is entirely internal to device 100.

Some embodiments may include a method implementable in a digital scale or other suitable weight-measuring device. The method may include, for example: optionally, storing in a local database, data indicating dosage of one or more medicaments; measuring the weight of a user (e.g., who may step on the digital scale); performing a local query to a locally-stored medicament database, and/or performing a remote query to a remotely-stored medicament database, in order to determine the suitable dosage, based on the measured weight, for one or more medicaments; conveying to the user (e.g., by displaying, or via audio output or speech output), for example, the user's measured weight as well the name of one or more medicaments and the suitable dosage (based on the user's measured weight) of those one or more medicaments. Other suitable operations may be performed.

Discussions herein utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

The terms "plurality" or "a plurality" as used herein include, for example, "multiple" or "two or more". For example, "a plurality of items" includes two or more items.

Some embodiments may take the form of an entirely hardware embodiment, an entirely software embodiment, or an embodiment including both hardware and software elements. Some embodiments may be implemented in software, which includes but is not limited to firmware, resident software, microcode, or the like.

Furthermore, some embodiments may take the form of a computer program product accessible from a computer-usable or computer-readable medium providing program code for use by or in connection with a computer or any instruction execution system. For example, a computer-usable or computer-readable medium may be or may include any apparatus that can contain, store, communicate, propagate, or transport the program for use by or in connection with the instruction execution system, apparatus, or device.

In some embodiments, the machine-readable or computer-readable or device-readable medium may be or may include an electronic, magnetic, optical, electromagnetic, InfraRed (IR), or semiconductor system (or apparatus or device) or a propagation medium. Some demonstrative examples of a computer-readable medium may include a semiconductor or solid state memory, magnetic tape, a removable computer diskette, a Random Access Memory (RAM), a Read-Only Memory (ROM), a rigid magnetic disk, an optical disk, or the like. Some demonstrative examples of optical disks include Compact Disk-Read-Only Memory (CD-ROM), Compact Disk-Read/Write (CD-R/W), DVD, or the like.

In some embodiments, a data processing system suitable for storing and/or executing program code may include at least one processor or controller or circuitry which may be coupled directly or indirectly to memory elements, for example, through a system bus. The memory elements may include, for example, local memory employed during actual execution of the program code, bulk storage, and cache memories which may provide temporary storage of at least some program code in order to reduce the number of times code must be retrieved from bulk storage during execution.

In some embodiments, input/output or I/O devices or components (including but not limited to keyboards, displays, pointing devices, etc.) may be coupled to the system either directly or through intervening I/O controllers. In some embodiments, network adapters may be coupled to the system to enable the data processing system to become coupled to other data processing systems or remote printers or storage devices, for example, through intervening private or public networks. In some embodiments, modems, cable modems and Ethernet cards are demonstrative examples of types of network adapters. Other suitable components may be used.

Some embodiments may be implemented by software, by hardware, or by any combination of software and/or hardware as may be suitable for specific applications or in accordance with specific design requirements. Some embodiments may include units and/or sub-units, which may be separate of each other or combined together, in whole or in part, and may be implemented using specific, multi-purpose or general processors or controllers. Some embodiments may include buffers, registers, stacks, storage units and/or memory units, for temporary or long-term storage of data or in order to facilitate the operation of particular implementations.

Some embodiments may be implemented, for example, using a machine-readable medium or article which may store an instruction or a set of instructions that, if executed by a machine, cause the machine to perform a method and/or operations described herein. Such machine may include, for example, any suitable processing platform, computing platform, computing device, processing device, electronic device, electronic system, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit; for example, memory, removable or non-removable media, erasable or non-erasable media, writeable or re-writeable media, digital or analog media, hard disk drive, floppy disk, Compact Disk Read Only Memory (CD-ROM), Compact Disk Recordable (CD-R), Compact Disk Re-Writeable (CD-RW), optical disk, magnetic media, various types of Digital Versatile Disks (DVDs), a tape, a cassette, or the like. The instructions may include any suitable type of code, for example, source code, compiled code, interpreted code, executable code, static code, dynamic code, or the like, and may be implemented using any suitable high-level, low-level, object-oriented, visual, compiled and/or interpreted programming language, e.g., C, C++, Java, BASIC, Pascal, Fortran, Cobol, assembly language, machine code, or the like.

Functions, operations, components and/or features described herein with reference to one or more embodiments, may be combined with, or may be utilized in combination with, one or more other functions, operations, components and/or features described herein with reference to one or more other embodiments, or vice versa.

While certain features of some embodiments have been illustrated and described herein, many modifications, substitutions, changes, and equivalents may occur to those skilled in the art. Accordingly, the claims are intended to cover all such modifications, substitutions, changes, and equivalents.

What is claimed is:

1. A digital bathroom scale, comprising:
a weight measuring unit internal to the digital bathroom scale, and comprising one or more load cells to measure a weight of a user who stands on the digital bathroom scale;
a dosage determination module internal to the digital bathroom scale, to determine a dosage of a medicament based on said weight of said user measured by the weight measuring unit;
a display unit embedded in the digital bathroom scale, to display to the user said dosage of said medicament,
wherein the digital bathroom scale is an integrated, autonomous device which is able (A) to measure the weight of the user who stands on the digital bathroom scale, and (B) to determine and display to the user the dosage of said medicament based on the weight of the user;
wherein the display unit is to display (a) the weight of the user as measured by the weight measuring unit, and (b) a name of said medicament, and (c) said dosage of said medicament as determined by the dosage determination module based on said weight.

2. The digital bathroom scale of claim 1,
wherein the display unit is to concurrently display (a) the weight of the user measured by the weight measuring unit, (b) the name of said medicament, (c) the dosage of said medicament determined by the dosage determination module based on said weight, (d) a name of another medicament, and (e) a dosage of said other medicament determined by the dosage determination module based on said weight.

3. The digital bathroom scale of claim 1, comprising:
a memory unit to store data representing (A) names of a plurality of medicaments, and (B) dosing information items corresponding to said plurality of medicaments.

4. The digital bathroom scale of claim 1, comprising:
an input unit to allow a user to select a particular medicament name from said names of medicaments;
wherein the dosage determination module is to determine a recommended dosage of said particular medicament based on the weight of the user measured by the weight measuring unit;
wherein the display unit is to display said recommended dosage of said particular medicament to the user.

5. The digital bathroom scale of claim 4, wherein the input unit comprises:
a microphone to receive a spoken utterance of the user, the utterance indicating said particular medicament name;
wherein the digital bathroom scale further comprises a processor to process said spoken utterance and to extract said particular medicament name from said spoken utterance.

6. The digital bathroom scale of claim 4, comprising:
a wireless transceiver to receive, via a wireless communication link, one or more updates to said data stored in said memory unit.

7. The digital bathroom scale of claim 4, comprising:
a communication port to receive, via a wired communication link, one or more updates to said data stored in said memory unit.

8. The digital bathroom scale of claim 1, comprising:
a wireless transceiver to (i) send a query to a remote server, the query indicating (A) a user-selected medicament, and (B) the weight of the user as measured by the weight measuring unit; and (ii) receive from the remote server a response indicating a particular dosage of said user-selected medicament corresponding to said weight of the user.

9. The digital bathroom scale of claim 1, comprising:
a wireless transceiver to (i) send to a remote server a query indicating a user-selected medicament; and (ii) receive from the remote server a response indicating dosage information of said user-selected medicament corresponding to two or more weight range values;
wherein the dosage determination module is to determine a recommended dosage of said user-selected medicament, based on (A) the weight of the user as measured by the weight measuring unit, and (B) the dosage information corresponding to the two or more weight range values received from the remote server.

10. The digital bathroom scale of claim 1, comprising:
a processor (A) to obtain local dosage information for a particular user-selected medicament based on a first, local, query towards a locally-stored medicament database internal to the digital bathroom scale; (B) to obtain remote dosage information for said particular user-selected medicament based on a second, remote, query towards a remotely-stored medicament database external to the digital bathroom scale; and (C) to transfer at least one of the local dosage information and the remote dosage information to the dosage determination module.

11. The digital bathroom scale of claim 1, comprising a single housing encapsulating the weight measurement unit, the dosage determination module, and the display unit.

12. The digital bathroom scale of claim 1, wherein the weight measurement unit is non-detachable from the dosage determination module.

13. The digital bathroom scale of claim 1, wherein the weight measurement unit is to transfer a value indicating the weight of the user to the dosage determination module via a wired link which is entirely internal to the digital bathroom scale.

14. The digital bathroom scale of claim 1, wherein the dosage determination module is to determine said dosage based exclusively on data stored internally within said digital bathroom scale, and without receiving wireless communication signals.

15. The digital bathroom scale of claim 1, wherein the dosage determination module is to determine said dosage based on a dual-query process which comprises both a local query to a locally-stored medicament database and a remote query to a remotely-stored medicament database.

16. The digital bathroom scale of claim 1, wherein the weight measuring unit is non-detachable and non-separable from the dosage determination module; wherein the weight measuring unit is hard-wired via circuitry to the dosage determination module.

17. The digital bathroom scale of claim 1, wherein the weight measuring unit is to transfer a value, indicating the weight of the user, to the dosage determination module via a wired link which is entirely internal to the digital bathroom scale.

18. The digital bathroom scale of claim 1, further comprising:
a parent-with-child button to be actuated by a user, indicating to the digital bathroom scale to perform a multi-step process for weighting a child;
wherein, in said multi-step process, the weight measuring unit is (a) to measure a weight (W2) of a parent, (b) to measure a combined weight (W1) of said parent holding said child, and (c) to determine a net weight of said child by subtracting the weight (W2) of the parent from the combined weight (W1) of the parent and the child;

wherein the display unit is to display (i) said net weight of the child, and (ii) dosage information for a pediatric medicament calculated based on said net weight of the child.

19. The digital bathroom scale of claim 1, further comprising:

a barcode scanner to scan a barcode printed on a packaging of said medicament;

a medicament sensor to identify said medicament based on said barcode printed on said packaging;

a processor (a) to search, in a medicament database stored locally within the digital bathroom scale, a record corresponding to said medicament, and (b) to command the display unit to display a name of said medicament and dosing information for said medicament.

20. The digital bathroom scale of claim 1, further comprising:

a medicament sensor comprising a camera, (i) to capture a photograph of said medicament autonomously when said medicament is placed by the user in a field-of-view of said medicament sensor, and (ii) to identify said medicament based on Optical Character Recognition (OCR) of a name of said medicament which appears in said photograph;

a processor (A) to search, in a medicament database stored locally within the digital bathroom scale, a record corresponding to said medicament, and (B) to command the display unit to display a name of said medicament and dosing information for said medicament.

* * * * *